United States Patent [19]
Boivin et al.

[11] Patent Number: 5,248,773
[45] Date of Patent: Sep. 28, 1993

[54] 16-METHYL-Δ1,4-PREGNADIENE-3,20-DIONES

[75] Inventors: Jean Boivin, Forges les Bains; Christine Chauvet, Paris; Samir Zard, Gif sur Yvette, all of France

[73] Assignee: Roussel-UCLAF, France

[21] Appl. No.: 903,886

[22] Filed: Jun. 25, 1992

[30] Foreign Application Priority Data

Jun. 25, 1991 [FR] France ............... 91 07784

[51] Int. Cl.⁵ ............ C07J 43/00; C07J 17/00; C07J 5/00
[52] U.S. Cl. ............ 540/108; 540/113; 540/114; 540/116; 540/120; 552/600; 552/601; 552/602; 552/604; 552/587; 552/588; 552/589
[58] Field of Search ......... 552/600, 601, 602, 604, 552/587, 588, 589; 540/108, 113, 114, 116, 120

[56] References Cited
FOREIGN PATENT DOCUMENTS
0104054 3/1984 European Pat. Off. .
0148616 7/1985 European Pat. Off. .

OTHER PUBLICATIONS
J. Chem. Research Article 1985 (3 pages).

*Primary Examiner*—Marianne M. Cintins
*Assistant Examiner*—Kimberly J. Kestler
*Attorney, Agent, or Firm*—Bierman and Muserlian

[57] ABSTRACT

A compound of the formula

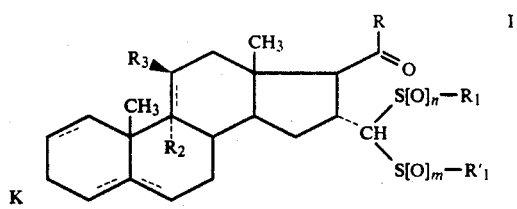

in which

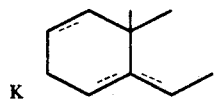

is either a 3-keto-Δ4-system or a 3-keto-Δ1,4-system or a 3-OR$_4$-Δ5-system in which R$_4$ is hydrogen or a protector group of hydroxy, R is methyl, —CH$_2$OH or —CH$_2$OR', in which R' is a protector group of hydroxy, R$_1$ and R'$_1$ are individually selected from the group consisting of methyl, a branched alkyl not possessing hydrogen in the $\beta$ position of 5 to 8 carbon atoms, aryl of up to 10 carbon atoms, heteroaryl of up to 10 carbon atoms and at least one heteroatom chosen from nitrogen, sulfur and oxygen and benzyl, n and m, are individually numbers 0 or 1, R$_2$ and R$_3$ are hydrogen or R$_2$ is fluorine and R$_3$ is formyloxy or acetyloxy and the dotted lines in position 9(11) indicate the optional presence of a second bond which are useful for the preparation of compounds of formula A.

7 Claims, No Drawings

16-METHYL-Δ1,4-PREGNADIENE-3,20-DIONES

OBJECTS OF THE INVENTION

It is an object of the invention to provide the novel compounds of formula I and a novel process and intermediates for their preparation.

It is another object of the invention to provide a novel process for the preparation of compounds of formula A.

These and other objects and advantages of the invention will become obvious from the following detailed description.

THE INVENTION

The novel compounds of the invention have the formula

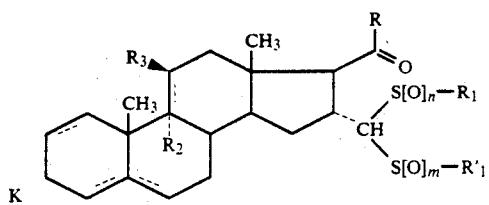

in which

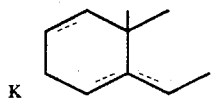

is either a 3-keto-Δ4-system or a 3-keto -Δ1,4-system or a 3-OR$_4$-Δ5-system in which R$_4$ is hydrogen or a protector group of hydroxy, R methyl, —CH$_2$OH or —CH$_2$—OR', in which R' is a protector group of hydroxy, R$_1$ and R'$_1$ are individually selected from the group consisting of methyl, a branched alkyl not possessing hydrogen in the β position of 5 to 8 carbon atoms, aryl of up to 10 carbon atoms, heteroaryl of up to 10 carbon atoms and at least one heteroatom chosen from nitrogen, sulfur and oxygen and benzyl, n and m, are individually numbers 0 or 1, R$_2$ and R$_3$ are hydrogen or R$_2$ is fluorine and R$_3$ is formyloxy or acetyloxy and the dotted lines in position 9(11) indicates the optional presence of a second bond.

R' is preferably a alkyl of 1 to 6 carbon atoms such as methyl, ethyl, propyl, isopropyl, butyl, isobutyl and tert-butyl, acyl of 1 to 6 carbon atoms such as formyl, acetyl, propionyl, butyryl and pivaloyl, aralkyl such as benzyl, tetrahydropyrannyl, an alkyl, aryl or arylalkyl silyl, preferably trimethyl silyl, tert-butyl dimethyl silyl, triphenyl silyl or diphenyl tert-butyl silyl. The above list of values of R' is not limitative and any protector group of the hydroxy known to a man skilled in the art, compatible with the operating conditions of the process defined above, is suitable.

When R$_1$ and R'$_1$ are alkyl of 5 to 8 carbon atoms, it is preferably neopentyl or a similar higher alkyl not possessing a hydrogen atom in the β-position. When R$_1$ and R'$_1$ are aryl, it is preferably phenyl, phenyl substituted by one or two methyls or naphthyl. When R and R'$_1$ are heteroaryl, it is preferably pyridyl, thiazolyl, or benzothiazolyl.

When R$_4$ is a protector group of hydroxy, it is notably one of the groups mentioned above for R'.

Among the preferred products of formula I are those of the formula

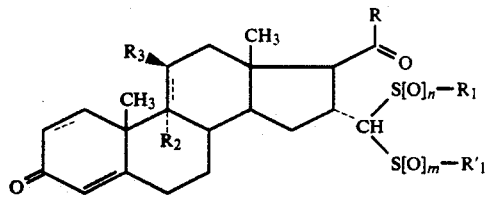

in which R, R$_1$, R'$_1$, R$_2$, R$_3$, m and n have the above meanings and the dotted lines in position 1(2) and 9(11) symbolize the optional presence of a second bond.

Among the preferred compounds of formula I are those wherein R is methyl, —CH$_2$OH or —CH$_2$OR' in which R' is alkyl of 1 to 4 carbon atoms, acyl of 1 to 5 carbon atoms or benzyl, R$_1$ and R'$_1$ are individually methyl, phenyl, tolyl or benzyl and n, m, R$_2$, R$_3$ and the dotted lines are defined as above.

Among the compounds of formula I are those of the formula

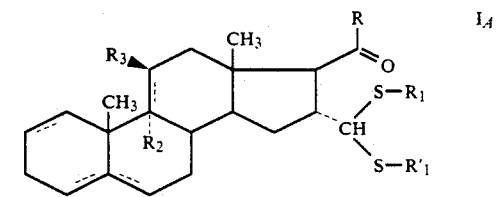

in which K, R, R$_1$, R'$_1$, R$_2$, R$_3$ and the dotted lines are defined as previously, the compounds of the formula

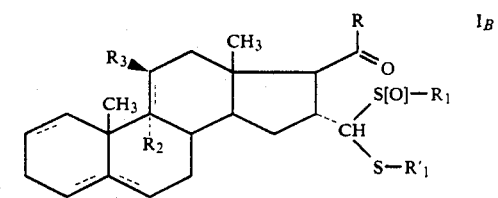

in which K, R, R$_1$, R'$_1$, R$_2$, R$_3$ and the doted lines are defined as previously and the compounds of the formula

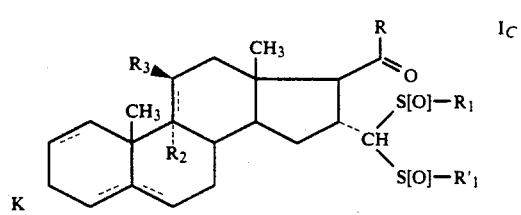

in which K, R, R$_1$, R'$_1$, R$_2$, R$_3$ and the dotted lines are defined as previously.

Among the preferred compounds of formula I are those wherein

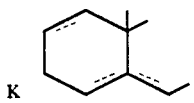

is a 3-keto-Δ1,4-system and R is —CH$_2$—OR', R' being defined as previously, R$_2$ and R$_3$ are hydrogen and the dotted lines in position 9(11) are a second bond.

Specific preferred compounds of formula I are 21-acetoxy-16α-[bis(phenylthio)-methyl]-Δ1,4,9(11)-pregnatriene-3,20-dione; 21-acetoxy-16α-[(phenylthio) (phenylsulfinyl)-methyl]-Δ1,4,9(11)-pregnatriene-3,20-dione and 21-acetoxy-16α-[bis(phenylsulfinyl)-methyl]-Δ1,4,9(11)-pregnatriene-3,20-dione.

The novel process of the invention for the preparation of a compound of formula I comprises reacting a compound of the formula

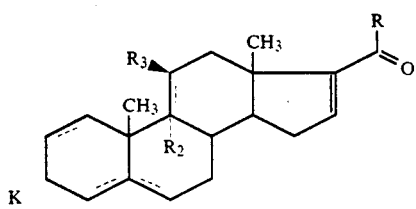

II in which K, R, R$_2$, R$_3$ and the dotted lines have the above meanings in a basic medium with a reagent of the formula

 P in which R$_1$ has the above meaning to obtain a compound of the formula

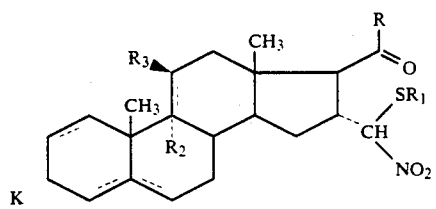

III in which K, R, R$_1$, R$_2$, P$_3$ and the dotted lines have the above meanings reacting the latter in the presence of an acid, with a thiol or thiophenyl of the formula

in which R'$_1$ has the above meaning to obtain a compound of the formula

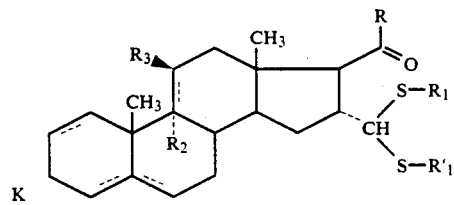

I$_A$ in which K, R, R$_1$, R'$_1$, R$_2$, R$_3$ and the dotted lines have the above meanings optionally reacting the latter with an equivalent of an oxidizing agent to obtain a compound of the formula

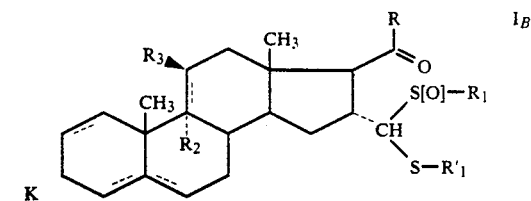

I$_B$ in which K, R, R$_1$, R'$_1$, R$_2$, R$_3$ and the dotted lines have the above meanings, or with at least two equivalents of an oxidizing agent to obtain a compound of the formula

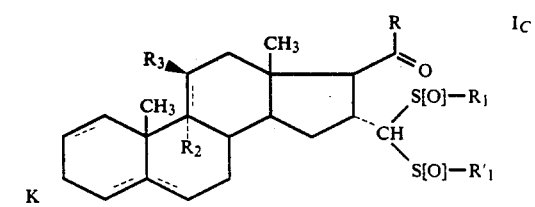

I$_C$ in which K, R, R$_1$, R'$_1$, R$_2$, R$_3$ and the dotted lines have the above A preferred mode of the process for preparing a compound of formula I comprises reacting a compound of the formula

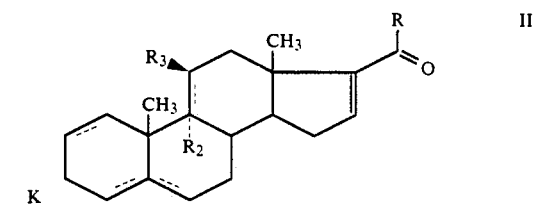

II in which K, R, R$_2$, R$_3$ and the dotted lines have the above meanings in a basic medium with a reagent of the formula

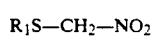 P in which R$_1$ has the above meaning to obtain a compound of the formula

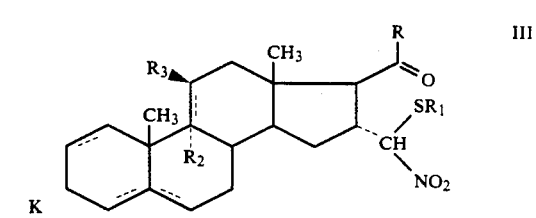

III in which K, R, R$_1$, R$_2$, R$_3$ and the dotted lines have the above meanings and reacting the latter in the presence of an acid with a thiol or a thiophenol of the formula

in which R'$_1$ has the above meaning to obtain a compound of the formula

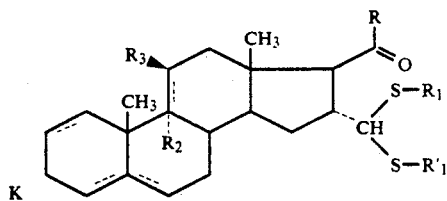

in which K, R, R$_1$, R'$_1$, R$_2$, R$_3$ and the dotted lines have the above meanings and reacting the latter with at least two equivalents of an oxidizing agent to obtain a compound of the formula

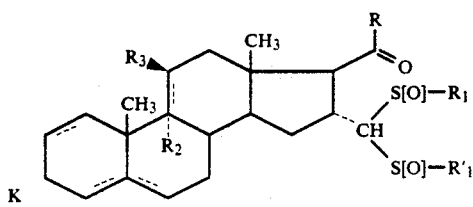

in which K, R, R$_1$, R'$_1$, R$_2$, R$_3$ and the dotted lines have the above meanings.

The action of the reagent of formula P with the compound of formula II is carried out in the presence of a base which can be an amino base such as a secondary or tertiary amine like diethylamine or triethylamine, diazabicycloundecene (DBU), diazabicyclononene (DBN), an acetate, a carbonate, a hydride, a hydroxide or an alkali metal alkoxide, the strong base being used preferably in a catalytic quantity.

The operation is carried out in an organic solvent such as an ether like tetrahydrofuran or dioxane, an alcohol like methanol or ethanol, an aromatic solvent like benzene or toluene, or dimethylforamide, dimethylsulfoxide or methylene chloride.

The action of the thiol or the thiophenol is catalyzed by an acid, preferbly a weak acid, which can be a carboxylic acid such as formic acid, acetic acid or propionic acid, a Lewis acid such as zinc chloride or aluminium chloride, or also phosphoric acid. The said acid can also, if desired, be used as the solvent. The solvent can also be an aromatic solvent such as benzene or toluene. The reaction conditions are chosen if appropriate so that they are compatible with the protector group of the hydroxy that can be carried by compound II and, more generally, with the structure of the molecule which one wishes to preserve. This is known to a man skilled in the art.

The oxidizing agent used to convert the compound of formula I$_A$ into the monosulfoxide or into the disulfoxide can be a peracid such as m-chloro perbenzoic acid, perbenzoic acid, perphthalic acid, the magnesium salt of monoperphthalic acid, or hydrogen peroxide in the presence of a carboxylic acid such as acetic acid, or a periodate, a perborate or a persulfate, preferably of sodium or potassium.

Also an object of the invention, as new industrial compounds are the compounds of formula III, as defined above.

The novel process of the invention for the preparation of a compound of the formula

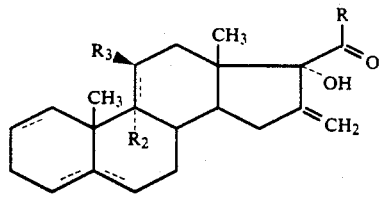

in which K, R, R$_2$, R$_3$ and the dotted lines have the above meanings comprises reacting a compound of formula I$_A$ with at least two equivalents of an oxidizing agent to obtain a compound of formula I$_C$ and reacting the latter hot with a thiophilic agent to obtain the expected compound of formula A or subjecting a compound of formula I$_C$ hot with a thiophilic agent to obtain the expected compound of formula A.

In a variation of the process to obtain a compound of formula A a compound of formula I$_B$ is heated optionally in the presence of a thiophilic agent to obtain a compound of the formula

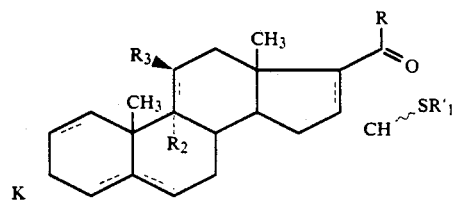

in which K, R, R'$_1$, R$_2$, R$_3$ and the dotted lines have the above meanings and the dotted line in position 16(17) and 16(16') symbolizes the existence of a vinyl and allyl sulfide mixture and the wavy line symbolizes the existence of a mixture of isomers, reacting the latter with at least one equivalent of an oxidizing agent to obtain a compound of the formula

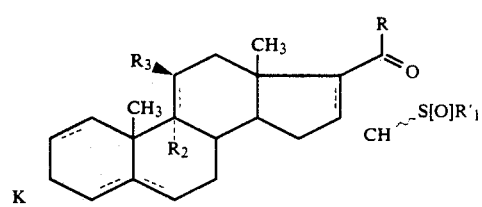

in which K, R, R'$_1$, R$_2$, R$_3$, the dotted lines and the wavy line have the above meanings and reacting the latter hot with a thiophilic agent to obtain the expected compound of formula A.

It is not necessary to isolate the disulfoxide of formula I$_C$ and a first -S[O]R$_1$ group can be removed therefrom by heating only to obtain the monosulfoxide of formula V and the second group can be removed by the sulfenate by hot reaction with a thiophilic agent to obtain the monosulfoxide of formula V with or without isolation. The compound of formula I$_B$ can be heated to eliminate the -S[O]R$_1$ and the compound of formula IV can be oxidized to form the compound of formula V.

The oxidizing agent used to convert the compound of formula I$_A$ into a compound of formula I$_C$, or to convert the compound of formula IV to a compound of formula V is one of those which have been mentioned above.

The thiophilic agent can be triphenylphosphine. trimethyl- or or triethylphosphine, triphenyl-, trimethylor triethylphosphite, dimethyl- or diethylphosphite, a secondary amine such as diethylamine, phosphorous acid, a thiol such as thiophenol or methyl mercaptan, or a thiosulfate, or a bisulfite, for example of sodium. Triphenylphosphine is particularly preferred.

The operation is carried out in an organic solvent or an organic solvent mixture, preferably at reflux. Examples of aromatic solvents are benzene, toluene, xylene, cyclohexane, tetrahydrofuran, dioxane, dimethoxyethane, monoglyme or diglyme, if appropriate mixed with a protic solvent, notably an alcohol such as methanol, ethanol or isopropanol.

The operation is carried out optionally in the presence of an alkaline carbonate such as sodium carbonate or calcium carbonate.

In the process of the invention, it is likely that during the process, the allyl form of the sulfoxide of formula V is found in equilibrium with the sulfenate form $V_a$:

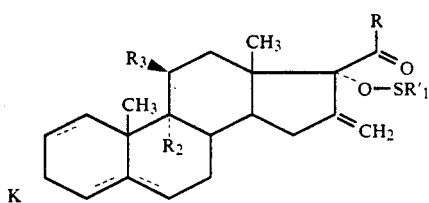

which undergoes a reduction to produce the desired compound (A).

In a preferred mode of the process, a compound of formula $I_A$ is reacted with at least two equivalents of an oxidizing agent to obtain a compound of formula $I_C$ and reacting the latter hot with a thiophilic agent to obtain the expected compound of formula A.

In another preferred mode of the process, a compound of formula $I_C$ is reacted hot with a thiophilic agent to obtain the desired compound of formula A.

It is possible to deprotect the products containing one or two protected hydroxys by using methods known to a man skilled in the art.

The novel industrial compounds useful as intermediates are the compounds of formula IV, as well as the compounds of the formula

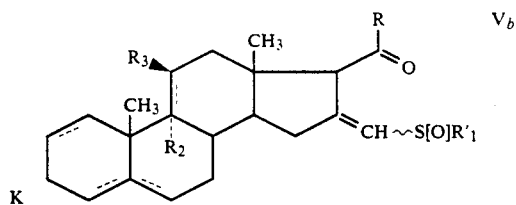

and the compounds of the formula

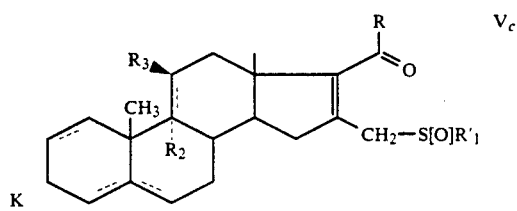

with the exception of those in which R is methyl, $R_2$ and $R_3$ are hydrogen and a double bond is present in position 9(11).

The compounds of formula A in which R is methyl are described in U.S. Pat. Nos. 3,354,184; 3,178,462; 3,312,692; 3,359,287; 3,064,015; and 3,519,619 or can be obtained from the compounds described in these Patents by known processes. Those in which R is free or protected —$CH_2OH$ are themselves described for example in the German Patents No. 1,263,765; No. 1,263,766, U.S. Pat. Nos. 3,350,394; 4,567,001; 3,354,184, French Patent No. 1,285,336 and European Patents No. 104,054 or No. 174,496, or can be obtained by known processes from compounds described in these Patents and U.S. Pat. Nos. 3,309,272 or 3,178,462.

The compounds of formula A are useful as intermediates in the synthesis of therapeutically active compounds.

The compounds of formula II in which R is methyl are described in U.S. Pat. Nos. 2,705,719; 2,817,671, French Patent No. 1,058,850; Belgian Patent No. 711,016 or English Patents No. 881,501; No. 2,199,325 or can be obtained from compounds described in these Patents, as well as in the German Patent No. 2,207,420 or U.S. Pat. Nos. 4,113,722 and 3,976,638, by processes known to a man skilled in the art. The compounds of formula II in which R is free or protected —$CH_2OH$ are described in U.S. Pat. Nos. 2,802,839; 2,745,852; 2,773,058; 2,864,834; Belgian Patents No. 540,478 or No. 789,387; German Patent No. 2,207,420; Dutch Patent No. 6,902,507 or Russian Patent No. 819,119, or can be obtained from the compounds described in these Patents, as well as in U.S. Pat. Nos. 3,976,638 or 2,966,504; European Patent No. 123,736 or Canadian Patent No. 760,431, by processes known to a man skilled in the art.

The reagents of formula P in which $R_1$ is methyl and phenyl are described in J. Chem. Soc. Chem. Comm. 1983, 835, 1978, 362 or also J. Org. Chem. 1978, Vol. 43, p. 3101. The other reagents of formula P can be prepared by similar methods to those described in the above references.

In the following examples, there are described several preferred embodiments to illustrate the invention. However, it is to be understood that the invention is not intended to be limited to the specific embodiments.

EXAMPLE 1

21-acetoxy-16α-[bis-(phenylthio)-methy]-Δ1,4,9(11)-pregonatriene-3,20-dione

STEP A: 21-acetoxy-16 α-[(phenylthio)-nitro-methy]-Δ1,4,9(11)-pregnatriene-3,20-dione 2.01 g of 21-acetoxy- Δ1,4,9(11)-16-pregnatetraen-3,20-dione and 1.1 g of (phenylthio)-nitro-methane were dissolved under inert atmosphere and in the shade in a mixture of 20 ml of dry THF and 20 ml of tert-butanol. 0.8 ml of DBU (1,8-diazabicyclo[5,4,0]undec-7-ene) were added and the reaction mixture was stirred at ambient temperature for 8 hours. A solution of 2 g of citric acid in 50 ml of water was added and after extraction with dichloromethane, filtering through silica, and drying over sodium sulfate, the solvent was filtered and evaporated under reduced pressure to obtain 3.73 g of crude product. The excess (phenylthio)-nitro-methane was eliminated by taking up the crude reaction product in a pentane (75 ml)—ether (30 ml) mixture to obtain 2.79 g of 21-acetoxy-16α-[(phenylthio)-nitro-methyl]-Δ1,4,9(11)-pregnatrien-3,20-dione melting at 92 to 100° C.

IR Spectrum (cm$^{-1}$): 1740(s); 1720(s); 1655(s); 1615(w); 1595(w); 1540(s); (NO$_2$); 885(w) (C—SPh)

NMR Spectrum $^1$H: 2 visible isomers: 0.72 and 0.73 (3H,s,Me-18); 1.41 (3H,s,Me-19); 2.17 and 2.20 (3H,s,COCH$_3$); 2.67 and 2.97 (1H, d, J=9.2 Hz,c c$_{17}$—H); 3.60 (1H,m,W$_{178}$ =35Hz, C$_{16}$—H); 4.43 and 4.75 (2H, AB system, J=16,9Hz) and 4.58 and 4.88 (2H, AB system, J=17,0 Hz); 5.38 (1H,d,J=8,14 Hz, C$_{16}'$—H) and 5.43 (1H,d,J=5,9 Hz, C$_{16}'$—H); 5.55(1H,massive, W$_{178}$ =10 Hz, C$_{11}$—H); 6.08 (1H, massive, W$_{178}$ =10 Hz, C$_4$—H); 6.30 (1H, d-d, J=10,2 Hz, J=1.7 Hz, C$_2$—H); 7.17 (1H,d,J=10,2 Hz, C$_1$—H), 7.34-7.48 (5H, massive).

NMR Spectrum $^{13}$C:
30 carbons, 2 isomers:
even: 29.87 and 30.65(s); 32.00(s); 34.60(s); 44.38 and 44.60(q); 45.91(q); 69.01(s); 130.58(q); 130.98(q); 143.21 and 143.34(q); 166.03(q); 170.40(q); 186.24(q); 201.40 and 201.65(q). odd: 13.64(p, 18-Me); 20.52 (p, COCH$_3$); 26.61 (p, 19-Me); 36.29(t); 40.05 and 40.17(t); 40.97(t); 52.21 and 52.62(t); 61.95(t); 98.03 and 98.54(t); 119.65(t); 124.18(t); 127.62(t); 129.71(t); 129.87(t); 132.94(t); 133.23(t); 154.17(t).

Mass Spectrum: m/z=512(M+); 483; 391; 314; 213.

STEP B: 21-acetoxy-16 α-[bis(phenylthio)-methy]-Δ1,4,9(11)-pregnatriene-3,20-dione 2 ml of thiophenol and 5 ml of acetic acid were mixed together and taken to boiling point under a nitrogen atmosphere. 2.51 g of 21-acetoxy-16α-[(phenylthio)-nitro-methyl]-Δ1,4,9(11)-pregnatrien -3,20-dione were added and the mixture was refluxed for 4 hours 30 minutes. Once the mixture had cooled down, 25 ml of ether were added. After neutralization of the acetic acid by a saturated solution of sodium bicarbonate, 25 ml of ether were added. The organic phase was washed with water, then dried and concentrated to obtain 4 g of a brown oil. The excess thiophenol was eliminated by taking up the crude reaction product in 25 ml of ether and 100 ml of pentane to obtain 1.70 g of the expected disulfide derivative melting at 98°-100° C. after purification by chromatography on silica (eluant: ether-dichloromethane 9-1) and having a specific rotation of $[\alpha]_D = -13.4°$ (C=12.7 mg/ml in chloroform).

IR Spectrum (cm$^{-1}$): 1750(s); 1720(s); 1665(s); 1630(m); 1610(W); 1585(W); 1550(W); 1480(w); 1440(w); 1410(w); 1370(w); 1270(w); 1120(W); 1155(w); 1070(m); 1050(m); 1025 (m); 890(m).

NMR Spectrum $^1$H: 0.61(3H,s,Me-18); 1.37(3H,s,Me-19); 2.10(3H,s, COCH$_3$); 2.87(1H, J=9,2Hz,C$_{17}$—H); 3.31(1H,m,W$_{178}$=19 Hz, C$_{16}'$—H); 4.25 and 4.68 (2H,AB system,J=16.9 Hz); 4.33(1H,d,J=4.8 Hz, C$_{16}'$—H); 5.47 (1H, massive, W$_{178}$ =9 Hz (C$_{11}$—H); 6.03(1H,massive, W$_{178}$ =5 Hz,C$_4$—H); 6.23(1H,d-d, J=10, 1 Hz, J=1.7 Hz, C$_2$—H); 7.10(1H,d,J=10,2 Hz, C$_1$—H), 7.18-7.41(10H, massive).

NMR Spectrum $^{13}$C:
even: 30.86(s); 32.14(s); 34.64(s); 40.23(s); 44.54(q); 134.40(q); 143.38(q); 154.45(q); 166.50(q); 170.32(q); 186.31(q); 202.50(q).

odd: 13.81(p); 20.53(p); 26.61(p); 36.50(t); 43.52(t); 45.98(t); 52.75(t); 62.47(t); 64.64(t); 69.09(t); 119.89(t); 124.03(t); 127.49(t); 127.88(t); 127.97(t); 129.16(t); 132.27(t); 132.57(t).

Mass Spectrum: m/z=489(M+ −Sph).

EXAMPLE 2

[21-acetoxy-16 α(phenylthio)-(phenyl-sulfinyl)-methyl]-Δ1,49(11) -preqnatriene-3,20-dione 60 mg of the disulfide of Example 1 were dissolved in 1 ml of dichloromethane and the mixture was cooled to −60° C. 26 mg of meta-chloroperbenzoic acid were added and after one hour, another 5 mg of meta-chloroperbenzoic acid were added. The reaction mixture stood at −60° C. for 1 hour and then 2 ml of a saturated solution of sodium bicarbonate were added. The mixture returned to ambient temperature and was extracted with dichloromethane (2×1.5 ml). The organic phase was washed with water (3×2 ml), then dried and the solvent was evaporated under reduced pressure to obtain 56 mg of the expected crude monosulfoxide. This derivative was unstable and was kept in a refrigerator.

EXAMPLE 3

21-acetoxy-16 α-[bis(phenylsulfinyl)-methyl]-Δ1,4,9(11)-pregnatriene-3,20-dione 1.09 g of the product of Example 1 were dissolved in 10 ml of dichloromethane and cooled to −78° C. 796 mg of meta chloroperbenzoic acid at 80% were added and the reaction mixture was held at −78° C. for 3 hours. 15 ml of a saturated solution of sodium bicarbonate were added and the mixture was immediately taken to ambient temperature and extracted with dichloromethane. The organic phase was washed with water, dried and the solvent was evaporated under reduced pressure. The disulfoxide obtained was purified by chromatography on silica (eluant: cyclohexane: ethyl acetate 1/1) to obtain 649 mg of the expected compound.

IR Spectrum cm$^{-1}$): 3050, 2960, 2920, 1745(s), 1720(s), 1660(s), 1625, 1615(m), 1580, 1450(m), 1375, 1320, 1270, 1240(s), 1150(m), 1090(m), 1050(m), 890.

NMR Spectrum $^1$H:
1st isomer: 0.62 (3H,s,Me-18); 1.40 (3H,s,Me-19); 2.18 (3H,s, COCH$_3$); 3.43-3.54 (3H,16-H,16'-H and 17-H); 4.29 and 4.59 (2H,AB system, J=16.6 Hz); 5.51 (1H,massive, W$_{\frac{1}{2}}$=10 Hz, C$_{11}$—H); 6.08 (1H,massive, W$_{178}$ =5 Hz, C$_4$—H); 6.28 (1H,d-d,J=10.2 Hz, J=1.7 Hz, C$_2$—H); 7.15 (1H,d, J=10,1 Hz,C$_1$H), 7.31-7,66 (10H, massive).

2nd isomer: 0.68(3H,s,Me-18); 1.40(3H,s,Me-19); 2.13(3H,s,COCH$_3$); 3.54-3.62(3H,16H, 16'-H and 17-H); 4.44 and 4.79(2H,AB system, J=16.5 Hz); 5.58(1H, massive, W$_{178}$ =10 Hz,C$_{11}$-H); 6.08 (1H,massive, W$_{178}$ 32 5 Hz,C<-H); 6.28(1H,dd,J=10.2 Hz, J=1.7 Hz,C$_2$—H); 7.18 (1H,d, J=10.1 Hz,C$_1$—H); 7.31-7.66(10H, massive).

EXAMPLE 3

1-acetoxy-16 α-(phenylthio)-(phenylsulfinyl)] and 16α[-bis (phenylsulfinyl)-methyl]-Δ1,4.9(11)-pregnatriene-3,20-dione 0.206 g of the disulfide of Example 1 were diluted with 2 ml of acetic acid under an argon atmosphere and the mixture was cooled to 0° C. using an ice bath. 5 drops of 30% hydrogen peroxide were added to the mixture and a few drops of dichloromethane were added. The mixture stood to allow the temperature to rise and after 21 hours at ambient temperature, a majority of the monosulfoxide was obtained which was identified by comparison with the product of Example 2. The reaction was continued for approximately 50 hours under an inert atmosphere and at ambient temperature, then stopped by the addition of water. After treatment as in Example 3, the expected disulfoxide was obtained which was identical to that of Example 3.

EXAMPLE 4

21-acetoxy-16-methylene-$\Delta$1,4,9(11)-pregnatriene-17$\alpha$-ol 3,20-dione

STEP A: 21-acetoxy-16 $\alpha$-(phenylthio)-methyl)]-$\Delta$1,4,9(11)-16-pregnatetraene-3,20-dione and the corresponding 16$\alpha$-(phenylthio)-methylene]derivative The monosulfoxide of Example 2 from 204 mg of disulfide was taken up in 3 ml of dry toluene. 101 mg of triphenylphosphine were added and the solution was refluxed under an argon atmosphere for 15 hours. After heating for 6 hours, 55 mg of triphenylphosphine were added and the toluene was evaporated off. The product was purified by chromatography on silica (eluant: cyclohexane/ethyl acetate 9/1 then 3/1) to obtain 143 mg of a mixture of two isomers of the position for the double bond in position 16 ($\Delta$16-16' or $\Delta$ 16-17).

IR Spectrum (cm$^{-1}$): 3020, 2910, 2820, 1750(s), 1720(m), 1660(s), 1620(m), 1580, 1550, 1430, 1370, 1260, 1040, 880.

NMR Spectrum $^1$H: 0.80(3H,s,Me-18); 1.41 and 1.42(3H,s,Me-19); 2.18 and 2.19(3H,s, COCH$_3$); 3.38(1H,m,W$_{178}$ =10 Hz, C$_{17}$—H); 3.72 and 4.09 (2H,AB system, J=13.6 Hz,C$_{16'}$—H); 4.44 and 4.67(2H,AB system, J=16.6 Hz) and 4.71 and 4.90 (2H,AB system, J=17 Hz); 5.50 and 5.59 (1H,massive,W$_{178}$ =12.5 Hz, C$_{11}$—H); 6.09(1H,massive, W$_{178}$ =5 Hz,c$_4$—H); 6.30(1H,d-d, J=10.2 Hz, J=1.7 Hz,C$_2$—H); 6.31 and 6.27(IH,d,J=1.9 Hz, C$_{16'}$—H), 7.16-7.52 (6H, massive).

NMR Spectrum $^{13}$C:
even: 32.03; 34.27; 34.66; 36.66; 37.12; 37.77; 40.41; 44.05; 45.97; 47.09; 68.08; 69.01; 134.58; 136.18; 143.06; 143.79; 144.11; 145.90; 151.58; 166.37; 170.29; 186.34; 193.57; 200.77.

Odd: 14.16; 16.02; 20.53; 26.54; 28.72; 35.73; 51.19; 63.20; 117.37; 119.84; 120.23; 123.97; 126.43; 127.43; 128.54; 129.02; 129.09; 131.72; 154.47.

Mass Spectrum: m/z=490, 489, 488(M+), 448, 447, 446(M+—COCH$_3$), 430, 415, 387, 319, 207.

STEP B: 21-acetoxy-16$\alpha$-[(phenylsulfinyl)-methyl]-$\Delta$1,4,9(11)-16-pregnatetraene-3,20-dione and the corresponding 16$\alpha$-[(phenylsulfinyl)-methylene]derivative 6.42 g of the mixture of isomers of Step A were dissolved in 100 ml of dichloromethane and the mixture was cooled to $-78°$ C. under a nitrogen atmosphere. 2.92 g of metachloroperbenzoic acid at 80% were added and the mixture was stirred for approximately 2 hours. The mixture was treated at low temperature with a saturated solution of sodium bicarbonate, then with water, followed by drying and evaporating to dryness. After chromatography on silica (eluant: ethyl acetate then ethyl acetate/methanol 9/1), 3.44 g of a mixture of the desired sulfoxides were obtained.

STEP C: 21-acetoxy-16-methylene-17 $\alpha$-hydroxy-$\Delta$1,4,9(11)-pregnatriene-3,20-dione The product of Step B was dissolved in a mixture of 50 ml of toluene and 50 ml of methanol and 2.68 g of triphenylphosphine were added. The mixture was heated at 85°-90° C. for 20 hours, then cooled and the solvent was evaporated. After chromatography on silica (eluant: ether/dichloromethane/petroleum ether 4/1/5), 1.97 g of the expected product were obtained melting at 213° to 215° C. (dec) after crystallization from methanol and having a specific rotation $[\alpha]_D = -32.8°$ (C=10.5 mg/ml in chloroform)

IR Spectrum (cm$^{-1}$): 3200; 2900; 2850; 2250; 1750(s); 1675(s); 1625; 1605; 1440; 1410; 1370; 1235(s); 1075; 915(s).

NMR Spectrum huH: 0.70(3H,s,Me-18); 1.41(3H,s,Me-19); 2.17(3H,s, COCH$_3$); 4.93 and 5.07(2H,AB system, J=17.6 Hz); 5.02(1H,s,c=CH$_2$); 5.15(1H,s,c=CH$_2$); 5.60(1H,massive, W$_{178}$ =12 Hz, C$_{11}$—H); 6.07(1H,massive, W$_{178}$ =5 Hz, C$_4$—H); 6.29(1H,d-d, J=10.2 Hz, J=1.4 Hz,Cz-H); 7.20(1H,d,J=10.2 Hz, C$_1$—H).

NMR Spectrum $^{13}$C:
even: 31.96(s); 32.25(s); 33.36(s); 35.05(s); 46.04(q); 45.45(q); 68.65(s); 89.65(q); 114.45(s); 142.28(q); 152.64(q); 166.49(q); 170.64(q); 186.37(q); 204.00(q).

odd: 14.18(p); 20.60(p); 26.81(p); 36.38(t); 46.31(t); 120.83(t); 124.05(t); 127.50(t); 154.51(t).

EXAMPLE 5

21-acetoxy-16-methylene-$\Delta$1,4,9(11)-pregnatriene-17$\alpha$-ol-3,20-dione 205 mg of the mixture of Step A of Example 4 were dissolved in 3 ml of dichloromethane and the mixture was cooled to $-78°$ C. under a nitrogen atmosphere. 91 mg of metachloroperbenzoic acid at 80% were added and after reacting for 2 hours, the starting product had completely disappeared. 221 mg of triphenyl phosphine were added at low temperature and then the dichloromethane was evaporated under reduced pressure. It was replaced by 3 ml of dry toluene and after 2 hours 30 minutes of reflux, evaporation to dryness took place to obtain after purification by chromatography on silica (eluant: cyclohexane/ether, 4/1 to 0/1), 113 mg of the expected alcohol which was identical to that obtained in Example 4 and melted at 213° C. to 215° C.

EXAMPLE 6

21-acetoxy-16-methylene-$\Delta$1.4.9(11)-pregnatriene-17$\alpha$-ol-3,20-dione 648 mg of the disulfoxide of Example 3 were dissolved under an argon atmosphere in 10 ml of toluene and the solution was cooled to $-60°$ C. 500 mg of calcium carbonate were added and the reaction mixture was heated to 80° C. for 2 hours. Then, 540 mg of triphenylphosphine and 10 ml of methanol were added. The solution was refluxed at 80° C for 11 hours, then cooled and evaporated to dryness. After chromatography on silica (eluant: cyclohexane/ethyl acetate; 7/3 then 1/1), 217 mg of the expected alcohol which was identical to that obtained in Example 4 and melted at 213° C. to 215° C. were obtained.

EXAMPLE 6'

21-acetoxy-16-methylene-Δ1,4,9(11)-pregnatriene-17α-ol-3,20-dione 287 mg of the disulfoxide of Example 3 or 3' were dissolved in 5 ml of dry toluene and 250 mg of calcium carbonate were added. The solution was refluxed for 75 minutes and 1 equivalent of trimethylphosphite and 5 ml of methanol were added. Then 8 drops of trimethylphosphine were added after 8 hours and after 24 hours. After 34 hours of reflux, it was observed by thin layer chromatography that the reaction was complete. The solution was allowed to cool and then 15 ml of dichloromethane and 15 ml of water were added. The mixture was filtered and the organic and aqueous phases were separated. The organic phase was washed with a saturated solution of sodium bicarbonate and a saturated solution of sodium chloride. After drying and eliminating the solvent, 256 mg of the crude expected product were obtained which was chromatographed on silica (eluant: petroleum ether/ethyl acetate 7/3 then 1/1) to obtain 64 mg which was 36% of the pure expected product which was identical to that of Example 4 and melted at 213° C. to 215° C.

EXAMPLE 7

21-acetoxy-16-methylene-Δ1,4,9(11)-pregnatriene-17α-ol-3,20-dione 702 mg of the product of Example 1 were dissolved under a nitrogen atmosphere in 10.5 ml of dichloromethane and the solution was cooled to −60° C. 319 mg of metachloroperbenzoic acid at 80% were added and after 30 minutes, another 243.6 mg of metachloroperbenzoic acid were added. The reaction stood between −60° C. and −40° C. for 5 hours and then 942 mg of triphenylphosphine were added. The dichloromethane was evaporated under reduced pressure and was replaced by 11 ml of dry toluene. The solution was refluxed for 7 hours and after cooling, the solvent was evaporated. The residue was chromatographed on a silica column (eluant: cyclohexane/ethyl acetate; 1/0 to 1/1 to obtain 115 mg of the expected alcohol which was identical to that of Example 4 and melted at 213° C. to 215° C.

EXAMPLE 8

16-methylene-Δ4-pregnen-17 α-ol-3,20-dione

STEP A:

16α-[(phenylthio)-nitro-methyl]-Δ4-pregnen-3,20-dione 138 mg of Δ4, 16-pregnadien-3,20-dione and 110 mg of (phenylthio)-nitro-methane were dissolved under an inert atmosphere and in the shade in 2 ml of a mixture (1-1) of tetrahydrofuran and tertiobutanol. Then 0.1 ml of DBU (1,8-diazabicyclo[5,4,0]undec-7-ene) were added and the reaction mixture was stirred at ambient temperature for 48 hours. A solution of 0.5 g of citric acid in 5 ml of water was added and after extraction with dichloromethane, drying over sodium sulfate, filtering and evaporating the solvent under reduced pressure, the residue was chromatographed on silica eluting with ether to obtain 48.3 mg of the expected product in the form of a 2-1 mixture of epimers melting at 166° C. to 172° C.

IR Spectrum (CHBr$_3$): 1702, 1660, 1551 cm$^{-1}$

NMR Spectrum (200 MHz): $^1$H: 7.4 (5H,m); 5.7 (1H,s); 5.4 (1H,2d); 3.55 (1H,m); 2.87 (1/3H,d, J-8.8Hz); 2.64 (2/3H,d, J=8.8Hz); 2.23 (2/3 3H,s); 2.16 (1/3 3H,s); 1.18 (3H,s); 0.71 (3H,s).

$^{13}$C (ppm): 14.38; 17.47; 21.04; 28.72; 29.23; 31.58; 31.76; 32.64; 34.00; 35.39; 35.83; 38.66; 38.76; 40.67; 45.23; 53.50; 54.75; 55.24; 66.86; 98.66; 98.99; 124.26; 129.53; 129.80; 131.45; 132.94; 170.18; 199.19; 206.37.

STEP B: 16-methylene- Δ4-pregnen-17α-ol-3,20-dione

Using the procedure of Example 3, the product of Step A was reacted to obtain the corresponding disulfoxide which was converted as indicated in Example 6 to obtain the expected 16-methylene- Δ4-pregen-17 α-ol-3,20-dione (obtained as indicated in U.S. Pat. No. 3,354,184).

EXAMPLE 9

3 β-acetoxy-16-methylene-Δ5-pregnen-17α-ol-3,20-dione

STEP A: 3 8-acetoxy-16 α-[(phenylthio)-nitro-methyl]-Δ5-pregnen -20-one 124.3 g of 3 β-acetoxy-Δ5-, 16-pregnadien-20-one and 89.7 mg of (phenylthio)-nitro-methane were dissolved under an inert atmosphere and in the shade in 2 ml of a (1-1) mixture of tetrahydrofuran and tertiobutanol. Then, 0.05 ml of DBU (1,8-diazabicyclo [5,4,0]undec-7-ene) were added and the reaction mixture was stirred at ambient temperature for 48 hours. A solution 0.5 g of citric acid in 5 ml of water was added and after extraction with dichloromethane, drying over sodium sulfate and filtering, the solvent was evaporated under reduced pressure. The residue was chromatographed on silica eluted with an ether-petroleum ether (1-3) mixture to obtain 66 mg of the expected product in the form of a 2-1 mixture of epimers .

IR Spectrum (CHBr$_3$) 1 1720, 1702, 1551 cm$^{-1}$

NMR Spectrum (200 MHz): $^1$H (Δ) 7.4 (5H,m); 5.35 (1H,2d); 4.6 (1H,m); 3.55 (1H,m); 2.85 (1/3H,d, J=8.8Hz); 2.64 (2/3H,d, J=8.8Hz); 2.23 (2/3 3H,s); 2.16 (1/3 3H,s); 2.04 (3H,s); 1.02 (3H,s); 0.66 (3H,s).

$^{13}$C (ppm): 14.19; 19.32; 20.88; 21.46; 27.72; 29.36; 31.53; 36.58; 36.96; 38.04; 38.72; 40.46; 45.19; 49.64; 55.34; 55.83; 66.90; 73.74; 98.73; 99.06; 121.96; 129.43; 129.71; 132.88; 139.72; 170.56; 206.64.

STEP B: 3 β-acetoxy-16-methylene- Δ5-pregnen-17 -ol-3.20-dione

Using the procedure of Example 3, the product of Step A was reacted to obtain the corresponding disulfoxide which was converted as indicated in Example 6 to obtain 38 -acetoxy-16-methylene-Δ5-pregen-17 α-ol-20-one (described in U.S. Pat. No. 3,519,619).

EXAMPLE 10

16-methylene- Δ4,9(11)-pregnadiene-17α-ol-3,20-dione

STEP A: 16 α-[(phenylthio)-nitromethyl-Δ4,9(11)-pregnadien-3,20-dione 100 mg of Δ4,9(11)-pregnatrien-3,20-dione and 100 mg of (phenylthio)-nitro-methane were dissolved under an inert atmosphere and in the shade in 1 ml of a (1-1) mixture of tetrahydrofuran and tertiobutanol. Then, 30 mg of DBU (1,8-diazabicyclo[5,4,0]undec-7-ene) were added and the reaction mixture was stirred at ambient temperature for 16 hours. A solution of 0.5 g of citric acid in 5 ml of water was added and after extraction with dichloromethane, drying over sodium sulfate and filtering, the solvent was evaporated under reduced pressure. The residue was chromatographed on silica eluting with a petroleum ether—ethyl acetate mixture (2-1) to obtain 129 mg of the expected product in the form of a 2-1 mixture of epimers.

IR Spectrum (CHBr$_3$) 1707, 1665, 1614, 1552 cm$^{-1}$

NMR Spectrum (200 MHz): $^1$H (Δ) 7.4 (5H,m); 5.75 (1H,s); 5.55 (1H,m); 5.4 (1H, 2d); 3.6 (1H,m); 2.95 (1/3H,d, J=9Hz); 2.75 (2/3H,d, J=9Hz); 2.24 (2/3 3H,s); 2.17 (1/3 3H,s); 1.34 (3H,s); 0.65 (3H,s). $^{13}$C (ppm): 13.96; 26.16; 29.50; 30.08; 31.28; 31.98; 32.60; 33.90; 34.25; 36.94; 40.70; 41.07; 43.30; 43.47; 51.58; 52.09; 66.50; 66.68; 98.46; 98.81; 117.84; 124.26; 129.41; 129.70; 132.81; 145.10; 198.70; 206.03.

STEP B: 16-methylene- Δ4,9(11)-pregnadien-17 α-ol-3,20-dione

Using the procedure of Example 3, the product of Step A was reacted to obtain the corresponding disulfoxide which was converted as indicated in Example 6 to obtain the expected 16-methylene-Δ4,9(11)-pregnadien-17 α-ol-3,20-dione (described in U.S. Pat. No. 3,359,287).

Various modifications of the compounds and method of the invention may be made without departing from the spirit or scope thereof and it is to be understood that the invention is intended to be limited only as defined in the appended claims.

What is claimed is:

1. A compound of the formula

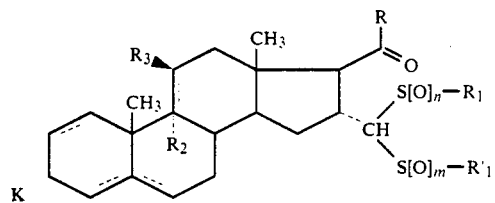

in which

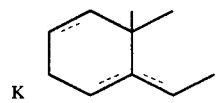

is either a 3-keto-Δ4-system or 3-keto-Δ1,4-system or a 3-OR$_4$-Δ5-system in which R$_4$ is hydrogen or a protector group of hydroxy, R is methyl, —CH$_2$OH or —CH$_2$OR', in which R' is a protector group of hydroxy, R$_1$ and R'$_1$ are individually selected from the group consisting of methyl, a branched alkyl of 5 to 8 carbon atoms not possessing hydrogen in the β position, aryl of up to 10 carbon atoms, heteroaryl of up to 10 carbon atoms and at least one heteroatom selected from the group consisting of nitrogen, sulfur and oxygen and benzyl, n and m, are individually the numbers 0 or 1, R$_2$ and R$_3$ are hydrogen or R$_2$ is fluorine and R$_3$ is formyloxy or acetyloxy and the dotted lines in position 9(11) indicate the optional presence of a second bond.

2. A compound of claim 1 wherin R is methyl or —CH$_2$OH or —CH$_2$R=, R' is alkyl of 1 to 4 carbon atoms or acyl of 1 to 5 carbon atoms or benzyl, R$_1$ and R'$_1$ are individually selected from the group consisting of methyl, phenyl, tolyl and benzyl and n, m, R$_2$ and R$_3$ have the definition of claim 1.

3. A compound of claim 1 having the formula

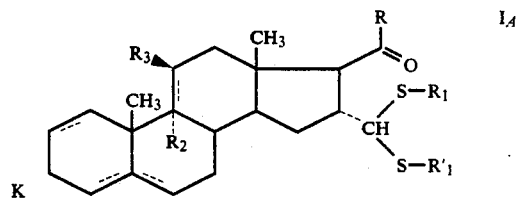

in which K, R, R$_1$, R'$_1$, R$_2$, R$_3$ and the dotted lines are defined as in claim 1.

4. A compound of claim, 1 having the formula

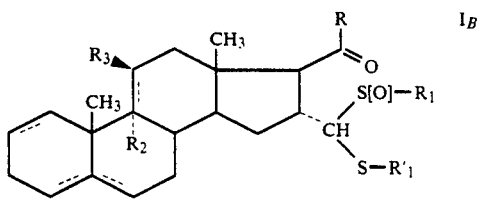

in which K, R, R$_1$, R'$_1$, R$_2$, R$_3$ and the dotted lines are defined as in claim 1.

5. A compound of claim 1 having the formula

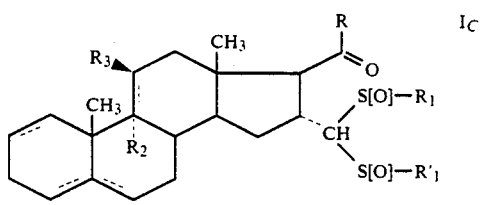

in which K, R, R$_1$, R'$_1$, R$_2$, R$_3$ and the dotted lines are defined as in claim 1.

6. A compound of claim 1 wherein

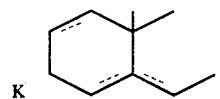

is a 3-keto-Δ1,4 system and R is —CH$_2$OR',R' being defined as in claim 2, R$_2$ and R$_3$ are hydrogen and the dotted lines in position 9(11) represent a second bond.

7. A compound of claim 1 selected from the group consisting of 21-acetoxy-16 α-[bis(phenylthio)-methyl]-Δ1,4,9(11)-pregnatriene-3,20-dione; 21-acetoxy-16α-[(phenylthio) (phenylsulfinyl)-methyl]-Δ1,4,9(11)-pregnatriene-3,20-dione and 21-acetoxy-16α-[bis(phenylsulfinyl)-methyl]-Δ1,4,9(11)-pregnatriene-3,20-dione.

* * * * *